(12) United States Patent
van den Honert (10) Patent No.: US 8,521,296 B2
(45) Date of Patent: Aug. 27, 2013

(54) SYSTEMS, METHODS, AND ARTICLES OF MANUFACTURE FOR CHARACTERIZING HEARING PROSTHESIS CHANNEL INTERACTION

(75) Inventor: Chris van den Honert, Englewood, CO (US)

(73) Assignee: Cochlear Limited, Macquarie University (AU)

( * ) Notice: Subject to any disclaimer, the term of this patent is extended or adjusted under 35 U.S.C. 154(b) by 53 days.

(21) Appl. No.: 13/185,376

(22) Filed: Jul. 18, 2011

(65) Prior Publication Data

US 2013/0023953 A1   Jan. 24, 2013

(51) Int. Cl.
*A61N 1/00* (2006.01)

(52) U.S. Cl.
USPC .......................................... 607/56

(58) Field of Classification Search
USPC ................................ 607/56, 45, 57
See application file for complete search history.

(56) References Cited

U.S. PATENT DOCUMENTS

| | | | |
|---|---|---|---|
| 6,167,138 A | 12/2000 | Shennib | |
| 2006/0100672 A1 | 5/2006 | Litvak | |
| 2007/0142874 A1* | 6/2007 | John | 607/45 |
| 2010/0198301 A1 | 8/2010 | Smith | |

FOREIGN PATENT DOCUMENTS

EP    1501333    1/2005

OTHER PUBLICATIONS

D.K. Eddington, et al., Auditory prostheses research with multiple channel intracochlear stimulation in man, Annals of Otology, Rhinology, and Laryngology, vol. 87, No. 6, Pt. 2, pp. 871-939 (Nov.-Dec. 1978).

M.L. Hughes and P.J. Abbas, The relation between electrophysiologic channel interaction and electrode pitch ranking in cochlear implant recipients, 119 J. Acoust. Soc. Am. 3, pp. 1527-1537 (Mar. 2006).

R.V. Shannon, Multichannel electrical stimulation of the auditory nerve in man. II. Channel interaction, Hearing Research, vol. 12, pp. 1-16 (1983).

G.S. Stickney, et al., Effects of electrode design and configuration on channel interactions, Hearing Research, vol. 211, pp. 33-45 (Dec. 9, 2005).

C.M. McKay, et al., Loudness summation for two channels of stimulation in cochlear implants: effects of spatial and temporal separation, Annals of Otology, Rhinology, and Laryngology, vol. 166, pp. 230-233 (Sep. 1995).

P.J. Abbas, et al., Channel interaction in cochlear implant users evaluated using the electrically evoked compound action potential, Audiol Neurootol, vol. 9, pp. 203-213 (Jul. 2004).

M. Chatterjee and R.V. Shannon, Forward masked excitation patterns in multielectrode electrical stimulation, 103 J. Acoust. Soc. Am. 5 (Pt. 1), pp. 2565-2572 (May 1998).

(Continued)

*Primary Examiner* — George Manuel
*Assistant Examiner* — Robert N Wieland
(74) *Attorney, Agent, or Firm* — McDonnell Boehnen Hulbert & Berghoff LLP (57) ABSTRACT

The present application discloses systems, methods, and articles of manufacture for characterizing hearing prosthesis channel interaction. Some embodiments may include applying a probe signal to a region of auditory neurons via a first hearing prosthesis channel, and applying a perturber signal to the region of auditory neurons via a second hearing prosthesis channel, where the perturber signal is configured to cause a polarity-independent neural excitation in an auditory neuron. Some embodiments may additionally include measuring one or more metrics corresponding to a neural response to the application of the probe and perturber signals.

30 Claims, 8 Drawing Sheets

(56) References Cited

OTHER PUBLICATIONS

M.L. Hughes and P.J. Abbas, Electrophysiologic channel interaction, electrode pitch ranking, and behavioral threshold in straight versus perimodiolar cochlear implant electrode arrays, 119 J. Acoust. Soc. Am. 3, pp. 1538-1547 (Mar. 2006).

J.A. Bierer and J.C. Middlebrooks, Cortical responses to cochlear implant stimulation: channel interactions, Journal of the Assoc. for Research in Otolaryngology, vol. 5, pp. 32-48 (Oct. 2003).

B.J. Kwon and C. van den Honert, Effect of electrode configuration on psychophysical forward masking in cochlear implant listeners, 119 J. Acoust. Soc. Am. 5 (Pt. 1), pp. 2994-3002 (May 2006).

J.C. Middlebrooks, Effects of cochlear-implant pulse rate and interchannel timing on channel interactions and thresholds, 116 J. Acoust. Soc. Am. 1, pp. 452-468 (Jul. 2004).

C. Boëx, et al., Electrical field interactions in different cochlear implant systems, 114 J. Acoust. Soc. Am. 4 (Pt. 1), pp. 2049-2057 (Oct. 2003).

C. de Balthasar, et al., Channel interactions with high-rate biphasic electrical stimulation in cochlear implant subjects, Hearing Research vol. 182, pp. 77-87 (Aug. 2003).

E. Favre and M. Pelizzone, Channel interactions in patients using the Ineraid multichannel cochlear implant, Hearing Research, vol. 66, pp. 150-156 (Apr. 1993).

J.C. Middlebrooks, Effects of cochlear-implant pulse rate and interchannel timing on channel interactions and thresholds. 116 J. Acoust. Soc. Am. 1, pp. 452-468 (Jul. 2004).

J.A. Bierer, Threshold and channel interaction in cochlear implant users: Evaluation of the tripolar electrode configuration, 121 J. Acoust. Soc. Am. 3, pp. 1642-1653 (Mar. 2007).

D.K. Eddington and M. Whearty, Electrode interaction and speech reception using lateral-wall and medial-wall electrode systems, 2001 Conference on Implantable Auditory Prostheses, Pacific Grove, CA., p. 49 (Aug. 2001).

PCT Search Report, PCT Application No. PCT/IB2012/053588, dated Jan. 31, 2013.

* cited by examiner

Article of Manufacture 900

Program Instructions 902

- Cause a hearing prosthesis to apply a probe signal to a region of auditory neurons via a first channel of the hearing prosthesis

- Cause the hearing prosthesis to apply a perturber signal to the region of auditory neurons via a second channel of the hearing prosthesis, wherein the perturber signal is configured to cause a polarity-independent neural excitation in an auditory neuron

- Receive at least one recorded metric corresponding to a neural response to the application of the probe and perturber signals

- Analyze the at least one recorded metric

Computer Readable Medium 903

Computer Recordable Medium 904

FIG. 9

SYSTEMS, METHODS, AND ARTICLES OF MANUFACTURE FOR CHARACTERIZING HEARING PROSTHESIS CHANNEL INTERACTION

BACKGROUND

Various types of hearing prostheses may provide persons with different types of hearing loss with the ability to perceive sound. Hearing loss may be conductive, sensorineural, or some combination of both conductive and sensorineural hearing loss. Conductive hearing loss typically results from a dysfunction in any of the mechanisms that ordinarily conduct sound waves through the outer ear, the eardrum, or the bones of the middle ear. Sensorineural hearing loss typically results from a dysfunction in the inner ear, including the cochlea where sound vibrations are converted into neural signals, or any other part of the ear, auditory nerve, or brain that may process the neural signals.

Persons with some forms of conductive hearing loss may benefit from hearing prostheses, such as acoustic hearing aids or vibration-based hearing aids. An acoustic hearing aid typically includes a small microphone to detect sound, an amplifier to amplify certain portions of the detected sound, and a small speaker to transmit the amplified sounds into the person's ear. Vibration-based hearing aids typically include a small microphone to detect sound, and a vibration mechanism to apply vibrations corresponding to the detected sound to a person's bone, thereby causing vibrations in the person's inner ear, thus bypassing the person's auditory canal and middle ear. Vibration-based hearing aids may include bone anchored hearing aids, direct acoustic cochlear stimulation devices, or other vibration-based devices. A bone anchored hearing aid typically utilizes a surgically-implanted mechanism to transmit sound via direct vibrations of the skull. Similarly, a direct acoustic cochlear stimulation device typically utilizes a surgically-implanted mechanism to transmit sound via vibrations corresponding to sound waves to generate fluid motion in a person's inner ear. Other non-surgical vibration-based hearing aids may use similar vibration mechanisms to transmit sound via direct vibration of teeth or other cranial or facial bones.

Persons with certain forms of sensorineural hearing loss may benefit from cochlear implants and/or auditory brainstem implants. For example, cochlear implants may provide a person having sensorineural hearing loss with the ability to perceive sound by stimulating the person's auditory nerve via an array of electrodes implanted in the person's cochlea. An external component of the cochlear implant detects sound waves, which are converted into a series of electrical stimulation signals delivered to the implant recipient's cochlea via the array of electrodes. Auditory brainstem implants may use technology similar to cochlear implants, but instead of applying electrical stimulation to a person's cochlea, auditory brainstem implants apply electrical stimulation directly to a person's brain stem, bypassing the cochlea altogether. Electrically stimulating auditory nerves in a cochlea with a cochlear implant or electrically stimulating a brainstem may enable persons with sensorineural hearing loss to perceive sound.

The effectiveness of any of the above-described hearing prostheses depends not only on the design of the particular prosthesis but also on how well the prosthesis is configured for or "fitted" to a prosthesis recipient. The fitting of the prosthesis, sometimes also referred to as "programming" or "mapping," creates a set of configuration settings and other data that defines the specific characteristics of the signals (acoustic, mechanical, or electrical) delivered to the relevant portions of the person's outer ear, cranial or facial bones, teeth, middle ear, inner ear, cochlea, brainstem, etc. One aspect of fitting some hearing prostheses to a specific prosthesis recipient may include identifying or characterizing various hearing prosthesis performance or operational metrics that may be particular to the specific prosthesis recipient, and fine-tuning the prosthesis configuration settings based on the performance or operational metrics.

SUMMARY

The present application discloses systems, methods, and articles of manufacture for identifying and/or characterizing hearing prosthesis channel interaction. In some embodiments, identifying and/or characterizing channel interaction may be helpful in determining various configuration settings of a hearing prosthesis during the fitting process.

Some embodiments may include generating a probe signal and a perturber signal. The probe signal may be similar to a standard stimulation signal typically generated by the hearing prosthesis. The perturber signal may be configured to cause a polarity-independent neural excitation in auditory neurons. The probe signal may be applied to a set of auditory neurons via a first hearing prosthesis channel, and the perturber signal may be applied to the auditory neurons via a second hearing prosthesis channel. The first channel of the hearing prosthesis may include one or more active electrodes and one or more reference electrodes. Similarly, the second channel of the hearing prosthesis may include one or more active electrodes and one or more reference electrodes.

The perturber signal may take a variety of forms. In some embodiments, the perturber signal may have a corresponding frequency that is greater than about 20 kHz. In some embodiments, the perturber signal may have a corresponding frequency that is between about 20 kHz and 55 kHz. However, other frequencies that may cause a polarity-independent neural excitation in the auditory neurons may be used as well. Similarly, the perturber signal may take the form of a rectangular waveform, a sinusoidal waveform, a triangular waveform, or other waveform. In some embodiments, the perturber signal may be amplitude modulated by at least one of a cosine onset ramp, a cosine offset ramp, a cosine squared ramp, a linear ramp, and/or a sigmoidal ramp.

In some embodiments, the probe signal and the perturber signal may be applied to auditory neurons in the prosthesis recipient's cochlea. The probe and perturber signals may be applied at substantially the same time in some embodiments. In other embodiments, the probe signal and the perturber signal may be applied at different times. The probe signal and the perturber signal in some embodiments may at least partially overlap in time. In other embodiments, the probe and perturber signals may not overlap in time. In some embodiments, the perturber signal may take the form of a single burst for a specific duration. In some embodiments, the perturber signal may include a plurality of bursts, where individual bursts may have a corresponding defined duration. Individual bursts may have substantially the same duration or different durations.

Some embodiments may additionally include characterizing the hearing prosthesis channel interaction with multiple perturber signals. For example, some embodiments may include generating multiple perturber signals configured to cause polarity-independent neural excitations, and applying the multiple perturber signals to the auditory neurons via multiple corresponding channels of the hearing prosthesis.

Because the perturber signal may be configured to cause a polarity-independent neural excitation in the auditory neurons, the interaction between the first channel and the second channel may be characterized by any of a plurality of different systems and methods. In some embodiments, the interaction between the first and second channels may be characterized or otherwise measured by recording one or more metrics corresponding to a neural response to the application of the probe and perturber signals. Such metrics may include behavioral feedback metrics from the prosthesis recipient, electrophysiological feedback metrics, a reflex measurement, and/or other measurements.

DETAILED DESCRIPTION

The following detailed description describes various features, functions, and attributes of the disclosed systems, methods, and articles of manufacture with reference to the accompanying figures. In the figures, similar symbols typically identify similar components, unless context dictates otherwise. The illustrative embodiments described herein are not meant to be limiting. Certain aspects of the disclosed systems, methods, and articles of manufacture can be arranged and combined in a wide variety of different configurations, all of which are contemplated herein.

For illustration purposes, some features and functions are described with respect to cochlear implants. However, many features and functions may be equally applicable to other types of hearing prostheses that may use multiple stimulation channels that might be susceptible to channel interference. Certain aspects of the disclosed systems, methods, and articles of manufacture could be applicable to any type of multi-channel hearing prosthesis now known or later developed that can be configured to stimulate the auditory neurons or the auditory nerve of a prosthesis recipient.

Cochlear Implant Overview

Figure 1:
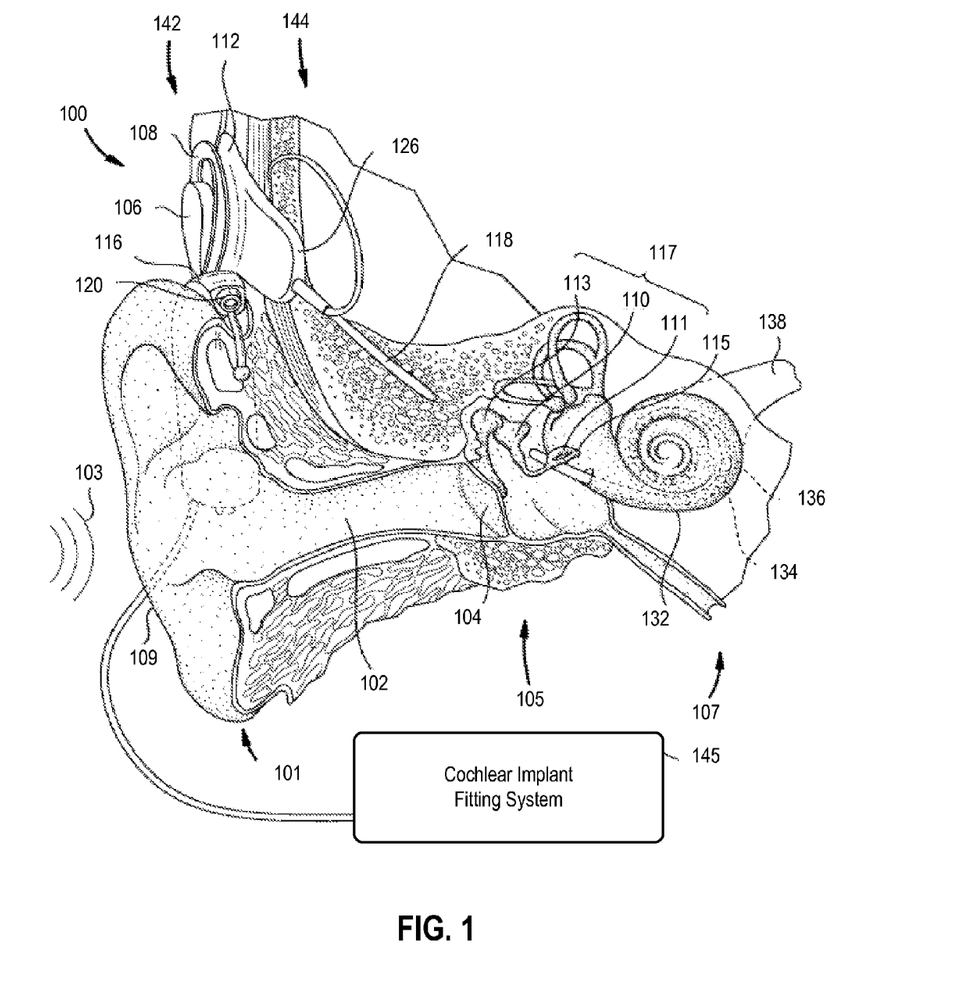
FIG. 1 shows one example of a cochlear implant that may be implanted into a hearing prosthesis recipient according to some embodiments of the disclosed systems, methods, and articles of manufacture.

FIG. 1 shows one example of a cochlear implant 100 that may be implanted into a hearing prosthesis recipient according to some embodiments of the disclosed systems, methods, and articles of manufacture. Relevant components of the prosthesis recipient's outer ear 101, middle ear 105, and inner ear 107 are described herein, followed by a description of the cochlear implant 100.

For persons without certain types of hearing impairments, an acoustic pressure or sound wave 103 may be collected by the auricle 109 and channeled into and through the ear canal 102. The tympanic membrane 104 is located at the distal end of the ear canal 102. The tympanic membrane 104 vibrates in response to the acoustic wave 103.

The vibration of the tympanic membrane 104 is coupled to the oval window or fenestra ovalis 115 through three bones of the middle ear 105, collectively referred to as the ossicles 117, and including the malleus 113, the incus 110, and the stapes 111. For persons without certain types of hearing impairments, the bones 113, 110 and 111 of the middle ear 105 serve to filter and amplify the acoustic wave 103, causing the oval window 115 to articulate and/or vibrate. The vibration of the oval window 115 causes waves of fluid motion within the cochlea 132. This fluid motion within the cochlea 132, in turn, activates tiny hair cells (not shown) that line the inside of the cochlea 132. Activation of the hair cells inside the cochlea 132 causes nerve impulses to be transferred through the auditory neurons in the cochlea, to the auditory nerve 138, and then to the brain (not shown), where the nerve impulses are perceived as sound. But for persons with sensorineural hearing loss, a cochlear implant such as implant 100 may instead be used to electrically stimulate the auditory neurons.

The cochlear implant 100 may include an external component assembly 142 that is directly or indirectly attached to the body of the recipient, and an internal component assembly 144 that is temporarily or permanently implanted in the recipient.

The external assembly 142 may include a sound processing unit 116 and an external transmitter unit 106. The sound processing unit 116 may include a digital signal processor (not shown), a power source (not shown) to power the cochlear implant 100, and a sound transducer 120. The sound transducer 120 may be configured to detect sound and to generate an audio signal representative of the detected sound. In the example embodiment shown in FIG. 1, the sound transducer 120 is a microphone. In alternative embodiments, the sound transducer 120 may comprise, for example, more than one microphone, one or more telecoil induction pickup coils, or other devices now or later developed that may detect sound and generate electrical signals representative of the detected sound. In some embodiments, the sound transducer 120 may not be integrated into the sound processing unit 116, and may instead be a separate component of the external component assembly 142.

The external transmitter unit 106 may include an external coil 108 of a transcutaneous energy transfer system along with the associated circuitry to drive the coil. The external transmitter unit 106 may also preferably include a magnet (not shown) secured directly or indirectly to the external coil 108.

The sound processing unit 116 may be configured to process the output of the microphone 120 that is positioned, at least in the embodiment shown in FIG. 1, near the auricle 109 of the recipient. The sound processing unit 116 may be configured to generate coded electrical signals, referred to herein as stimulation signals (such as the probe signal and the perturber signals described herein) which can be provided to the external transmitter unit 106 via a cable (not shown). The sound processing unit 116 shown in this example embodiment is designed to fit behind the auricle 109. Alternative versions may be worn on or fully implanted in the body. Some fully implantable systems may incorporate the sound processing unit into the internal component assembly 144.

The internal component assembly 144 may include an internal receiver unit 112, a stimulator unit 126 and an electrode assembly 118. The internal receiver unit 112 and the stimulator unit 126 may be hermetically sealed within a biocompatible housing.

The internal receiver unit 112 may include an internal coil (not shown) of the transcutaneous transfer system, along with associated circuitry. The implanted internal receiver unit 112 may be positioned in a recess of the temporal bone adjacent to the outer ear 101 of the recipient, as shown in FIG. 1. The external coil 108 may be held in place and aligned with the implanted internal coil via magnets. In one embodiment, the external coil 108 may be configured to transmit electrical signals to the internal coil via a radio frequency (RF) link.

The electrode assembly 118 may be designed to extend from the stimulator unit 126 to the cochlea 132 and to terminate in an array 134 of electrodes 136. Stimulation signals, such as the probe signals and/or perturber signals described herein may be generated by the stimulator unit 126 and applied to the cochlea 132 via the electrodes 136. The electrodes 136 are configured to apply the stimulation signals to the prosthesis recipient's cochlea to cause neural excitations of the auditory neurons in the cochlea. These neural excitations are then transmitted to the recipient's brain via the auditory nerve 138 where they are interpreted by the prosthesis recipient as sound.

As shown in FIG. 1, the cochlear implant 100 may be further configured to interface with a cochlear implant fitting system 145. The cochlear implant fitting system 145 (or other hearing prosthesis fitting system) may be implemented with a computing device, such as a personal computer, workstation, handheld computing device, tablet computer, or other similar computing devices.

In some embodiments, the hearing prosthesis fitting system (such as the cochlear implant fitting system 145) may be configured to send commands to and receive data from a corresponding hearing prosthesis (such as cochlear implant 100). For example, in some embodiments, a hearing prosthesis fitting system may be configured to send data corresponding to the probe and/or perturber signals described herein to the hearing prosthesis. Similarly, the hearing prosthesis fitting system may additionally be configured to receive data from the hearing prosthesis, such as data related to electrophysiological measurements or other types of measurements described herein. In some embodiments, the hearing prosthesis fitting system may also be configured to analyze the data received from the hearing prosthesis and/or other sources.

Electric Stimulation of Auditory Neurons

As described above, the cochlear implant 100 may be configured to apply stimulation signals to auditory neurons in a recipient's cochlea. The stimulation signals may be applied via corresponding sets of electrodes. One set of electrodes configured to apply a stimulation signal may be referred to as a channel. Individual channels may include (i) one or more active electrodes configured as a current source and (ii) one or more reference electrodes configured as a current sink.

Figure 2:
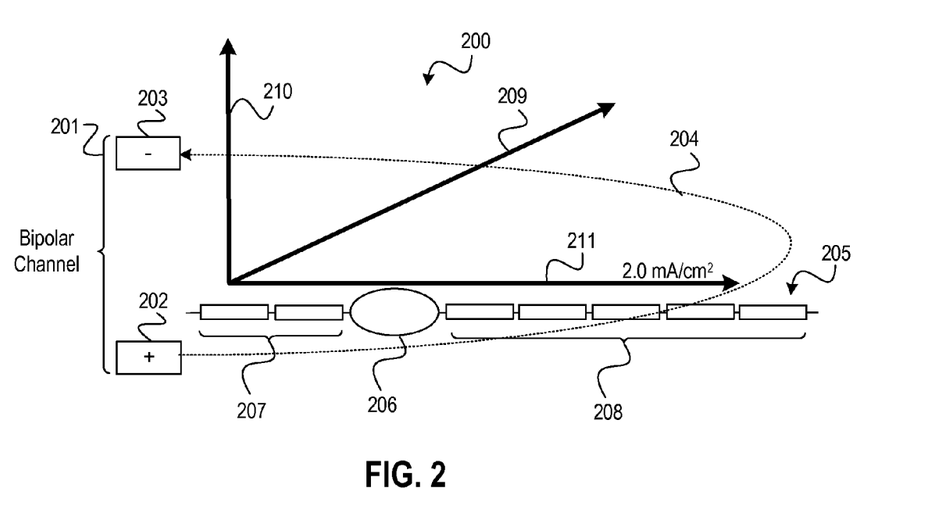
FIG. 2 shows an example of an auditory neuron in the presence of an electrical current corresponding to the application of a stimulation signal via a bipolar channel of a hearing prosthesis according to some embodiments of the disclosed systems, methods, and articles of manufacture.

FIG. 2 shows an example 200 of an auditory neuron 205 in the presence of an electrical current 204 corresponding to the application of a stimulation signal via a bipolar channel 201 of a hearing prosthesis, such as the cochlear implant 100 shown in FIG. 1. The auditory neuron 205 may include a cell body 206, a peripheral axon 207, and a central axon 208.

The channel 201 shown in FIG. 2 is considered a bipolar channel in part because it includes one active electrode 202 and one reference electrode 203. When a stimulation signal is applied via the bipolar channel 201, current 204 corresponding to the stimulation signal may flow from the active electrode 202 (the current source) to the reference electrode 203 (the current sink). In the example shown in FIG. 2, the current 204 flows across the auditory neuron 205 at an angle depicted by the arrow 209. The angle 209 of the current 204 flow may be represented as the combination of a longitudinal component 210 running perpendicular to the auditory neuron 205 and a radial component 211 running parallel to the auditory neuron 205.

In operation, the radial component 211 of the current 204 is most responsible for the neural excitation experienced by the auditory neuron 205 due to the stimulation signal. If the radial component 211 of the current 204 is of sufficient amplitude and duration, then the radial component 211 of the current 204 will depolarize the central axon 208 to the right of cell body 206 of the auditory neuron 205 sufficiently to cause a corresponding impulse signal in the auditory neuron 205. The impulse signal caused by the current 204 may be propagated to the implant recipient's brain (not shown) via the implant recipient's auditory nerve 138 (FIG. 1).

In the example shown in FIG. 2, the radial component 211 of the current 204 is 2.0 mA/cm$^2$. In this example, the radial component 211 of the current 204 may be of sufficient amplitude and duration to cause the auditory neuron 205 to become hyperpolarized near the peripheral axon 207 and depolarized near the central axon 208. The peripheral axon 207 on the left side of the cell body 206 of the nerve fiber that is hyperpolarized is inhibited from generating an impulse, while the central axon 208 on the right side of the cell body 206 that is depolarized may be excited, thus causing an impulse corresponding to the radial component 211 to propagate on the auditory neuron 205 from the central axon 208 on the right side of the cell body 206 to the brain.

In some embodiments with certain types of metal electrodes, the electric currents flowing between the metal electrodes 136 of the electrode array 134 (FIG. 1) may reverse direction from time to time to prevent conditions that may lead to electrolytic damage to both the electrodes and the surrounding tissue. When such reversal of current direction occurs, neural regions that were previously hyperpolarized may become depolarized, and vice versa. Thus, with reference to the example of FIG. 2, when current flow is reversed, neural excitation may occur at the peripheral axon 207, causing an impulse to propagate across the cell body 206 and along central axon 208 toward the brain.

Interaction Between Hearing Prosthesis Channels

Figure 3:
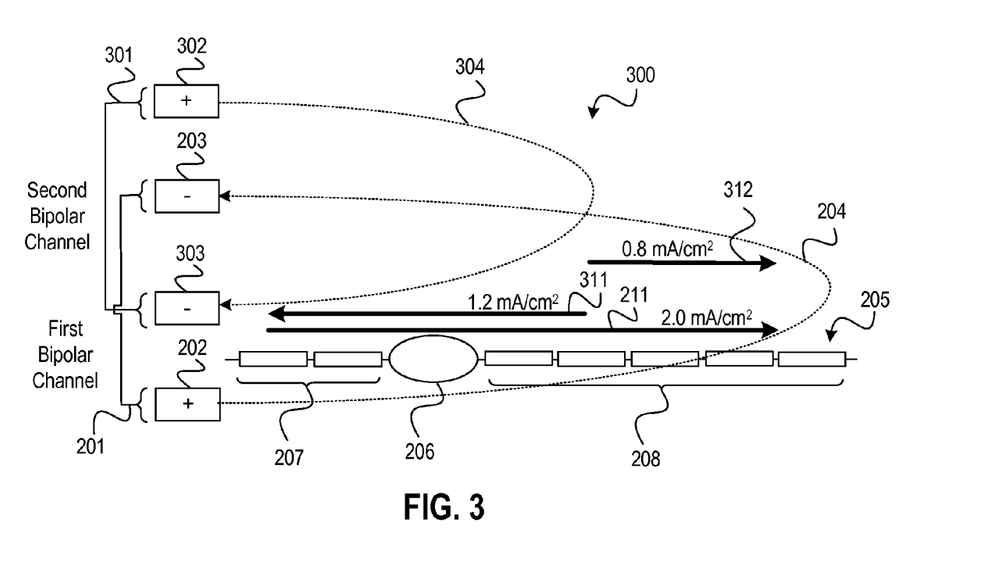
FIG. 3 shows an example of an auditory neuron in the presence of two stimulation signals applied via two corresponding bipolar channels of a hearing prosthesis according to some embodiments of the disclosed systems, methods, and articles of manufacture.

FIG. 3 shows an example of an auditory neuron 205 in the presence of two stimulation signals applied via two corresponding bipolar channels 201, 301 of the prosthesis according to some embodiments of the disclosed systems, methods, and articles of manufacture.

The first bipolar channel 201 shown in the example of FIG. 3 may be substantially similar to the bipolar channel 201 shown in the example of FIG. 2. In particular, the first bipolar channel 201 includes one active electrode 202 and one reference electrode 203. When a first stimulation signal is applied via the first bipolar channel 201, a current 204 corresponding to the first stimulation signal may flow from the active electrode 202 (the current source) to the reference electrode 203 (the current sink). In the example shown in FIG. 3, the radial component 211 (parallel to the auditory neuron 205) of the current 204 is 2.0 mA/cm$^2$ that flows from left-to-right, i.e., from the peripheral axon 207 to the central axon 208 of the auditory neuron 205.

The second bipolar channel 301 shown in the example of FIG. 3 may include one active electrode 302 and one reference electrode 303. When a second stimulation signal is applied via the second bipolar channel 301, current 304 corresponding to second stimulation signal may flow from the active electrode 302 (the current source) to the reference electrode 303 (the current sink). In the example shown in FIG. 3, the radial component 311 (parallel to the auditory neuron 205) of the current 304 is 1.2 mA/cm$^2$ that flows from right-to-left, i.e., from the central axon 208 to the peripheral axon 207 of the auditory neuron 205.

In operation, the auditory neuron 205 experiences the combination of: (1) the left-to-right-flowing 2.0 mA/cm$^2$ radial component 211 of the current 204 corresponding to the first stimulation signal; and (2) the right-to-left-flowing 1.2 mA/cm$^2$ radial component 311 of the current 304 corresponding to the second stimulation signal. Thus, because the right-to-left-flowing 1.2 mA/cm$^2$ radial component 311 of the current 304 corresponding to the second stimulation signal is in the opposite direction of the left-to-right flowing 2.0 mA/cm$^2$ radial component 211 of the current 204 corresponding to the first stimulation signal, the auditory neuron 205 experiences 0.8 mA/cm$^2$ of current that flows from left-to-right, i.e., from the peripheral axon 207 to the central axon 208 of the auditory neuron 205, shown as arrow 312.

In example 300 shown in FIG. 3, there is "interaction" between the first bipolar channel 201 and the second bipolar channel 301 in part because the current 304 corresponding to the second stimulation signal generated by the second bipolar channel 301 affects the current 204 corresponding to the first stimulation signal generated by the first bipolar channel 201 (and vice versa). In particular, the radial component 311 of the current 304 corresponding to the second stimulation signal from the second bipolar channel 301 cancels a portion of the radial component 211 of the current 204 corresponding to the first stimulation signal from the first bipolar channel 201. Because the current 304 reduces the effect that the current 204 has on the auditory neuron 205, the interaction between the first bipolar channel 201 and the second bipolar channel 301 is said to be "destructive." As a result, the auditory neuron 205 may experience a weaker neural excitation when the first stimulation signal and the second stimulation signal are both activated at the same time (or close to the same time) than when the first stimulation signal is activated alone.

In operation, such channel interaction may be undesirable. For example, the weaker current experienced by the auditory neuron 205 in the presence of the first and second stimulation signals may result in the prosthesis recipient experiencing a sound sensation that is lower than desired. Indeed, for some prosthesis recipients, the resulting 0.8 mA/cm$^2$ of example 300 may not be of sufficient amplitude to cause the auditory neuron 205 to become depolarized near the central axon 208, thus resulting in the prosthesis recipient not experiencing any sound sensation from the auditory neuron 205 when the first and second stimulation signals are activated at the same time (or close to the same time).

Additionally, the bipolar channel interaction illustrated in example 300 of FIG. 3 is polarity dependent. For example, if the polarity of the second bipolar channel 301 is reversed so that electrode 303 is the active electrode and electrode 302 is the reference electrode, then the 1.2 mA/cm$^2$ radial component of the current 304 corresponding to the second stimulation signal would flow left-to-right from the peripheral axon 207 to the central axon 208 instead of right-to-left from the central axon 208 to the peripheral axon 207 of the auditory neuron 205. In such an alternative configuration (not shown), the auditory neuron 205 might experience 3.2 mA/cm$^2$ corresponding to the arithmetic sum of the radial components of the currents corresponding to first and second stimulation signals. Because the current 304 increases the effect that the current 204 has on the auditory neuron 205, the interaction between the first bipolar channel 201 and the second bipolar channel 301 is said to be "constructive." As a result, the auditory neuron 205 may experience a stronger neural excitation when the first stimulation signal and the second stimulation signal are both activated at the same time (or close to the same time) than when the first stimulation signal is activated alone. The stronger current experienced by the auditory neuron 205 may result in the prosthesis recipient experiencing a sound sensation that is greater than desired. Indeed, for some prosthesis recipients, the 3.2 mA/cm$^2$ in such an alternative embodiment may result in an uncomfortably or even dangerously loud sound sensation.

Figure 4:
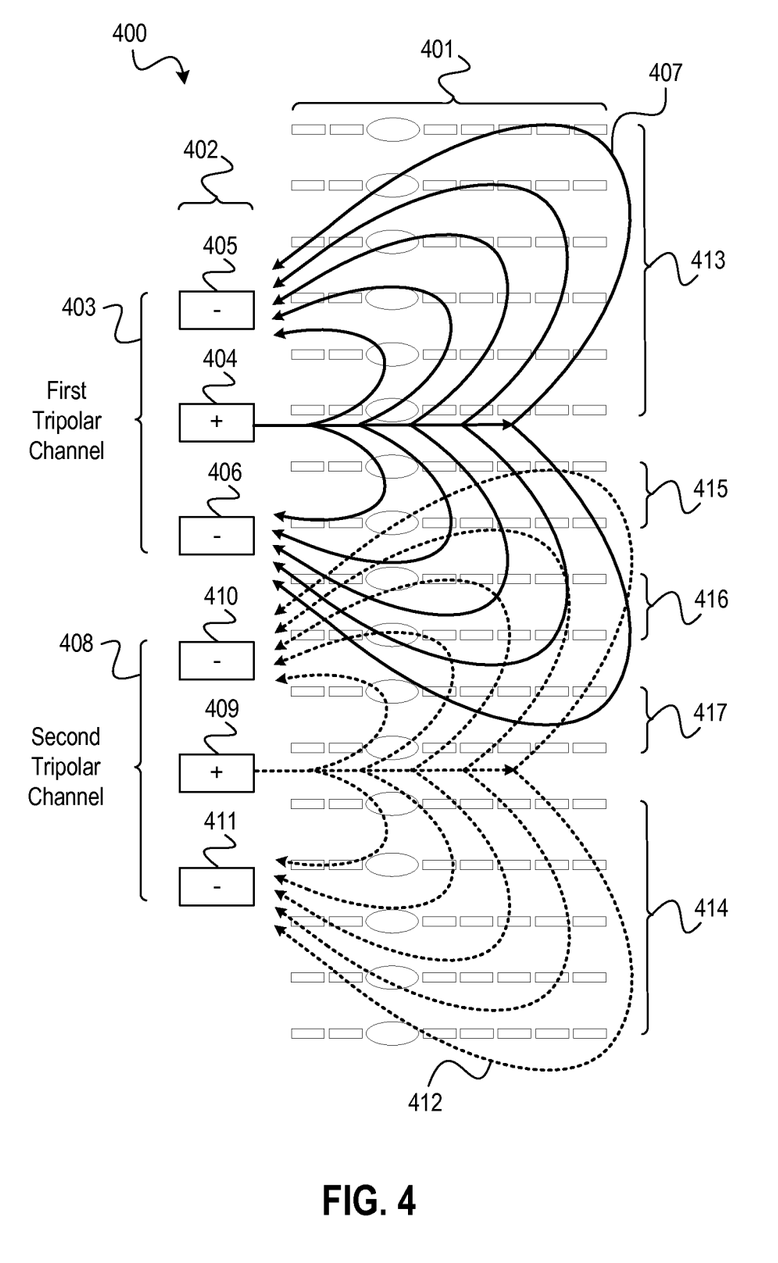
FIG. 4 shows an example of a collection of auditory neurons in the presence of currents corresponding to two stimulation signals via a collection of electrodes corresponding to two tripolar channels of the hearing prosthesis according to some embodiments of the disclosed systems, methods, and articles of manufacture.

The problem of stimulation channel interaction is even more complicated in more advanced channel configurations, such as tripolar and phased array channel configurations. For example, FIG. 4 shows an example 400 of a collection of auditory neurons 401 in the presence of currents corresponding to two stimulation signals applied via a collection of electrodes 402 corresponding to two tripolar channels 403, 408 of the hearing prosthesis according to some embodiments of the disclosed systems, methods, and articles of manufacture. The channels 403 and 408 are referred to as tripolar channels in part because each channel has three electrodes.

The first tripolar channel 403 includes one active electrode 404 and two reference electrodes 405, 406, and the second tripolar channel 408 includes one active electrode 409 and two reference electrodes 410, 411. However, other tripolar channel configurations may alternatively include two active electrodes and one reference electrode. The three electrodes of a particular tripolar channel may also be in different physical arrangements than the arrangement shown in example 400. In operation, the first tripolar channel 403 may be configured to apply a first stimulation signal to the set of auditory neurons 401, and the second tripolar channel 408 may be configured to apply a second stimulation signal to the set of auditory neurons 401.

For some of the auditory neurons 401 in example 400, the current 412 corresponding to the second stimulation signal may not interact with the current 407 corresponding to the first stimulation signal. For example, the auditory neurons 401 in the region 413 may be sufficiently far away from the current 412 corresponding to the second stimulation signal to experience no effect (constructive or destructive) from the current 412 corresponding to the second stimulation signal.

For other auditory neurons 401 in example 400, the current 412 corresponding to the second stimulation signal may destructively interfere with the current 407 corresponding to the first stimulation signal. For example, the auditory neurons in region 415 may experience a reduction in the left-to-right current flow caused by the current 407 corresponding to the first stimulation signal because of the right-to-left destructive interference caused by the current 412 corresponding to the second stimulation signal. Similarly, the auditory neurons in region 417 may experience a decrease in the right-to-left current flow caused by the current 407 corresponding to the first stimulation signal because of the left-to-right destructive interference caused by the current 412 corresponding to the second stimulation signal.

For still other auditory neurons 401 in example 400, the current 412 corresponding to the second stimulation signal may constructively interfere with the current 407 corresponding to the first stimulation signal. For example, the auditory neurons in region 416 may experience an increase in the right-to-left current flow caused by current 407 corresponding to the first stimulation signal because of the right-to-left constructive interference caused by the current 412 corresponding to the second stimulation signal.

In example 400, there is "interaction" between the first tripolar channel 403 and the second tripolar channel 408 in part because the current 412 corresponding to the second stimulation signal from the second tripolar channel 408 affects the current 407 corresponding to the first stimulation signal from the first tripolar channel 407 (and vice versa). In particular, the current 412 corresponding to the second stimulation signal from the second tripolar channel 408 constructively interferes with the current 204 corresponding to the first stimulation signal from the first tripolar channel 403 in some places, and the current 412 corresponding to the second stimulation signal from the second tripolar channel 408 destructively interferes with the current 204 corresponding to the first stimulation signal from the first tripolar channel 403 in some places. As a result, the auditory neurons 401 in the region surrounding the electrodes 402 of the first tripolar channel 403 and the second tripolar channel 408 may experience stronger and/or weaker neural excitations when the first stimulation signal and the second stimulation signal are both activated at the same time (or close to the same time) than when the first stimulation signal is activated alone.

As was the case with the bipolar channel example 300 shown in FIG. 3, the tripolar channel interaction illustrated in example 400 of FIG. 4 is polarity dependent. For example, if the polarity of the second tripolar channel 408 is changed so that electrode 410 is the active electrode and electrodes 409 and 411 are the reference electrodes, then the neural excitation experienced by the auditory neurons may be different than previously described. In operation, these different neural excitations may result in lower and/or higher than desired sound sensations.

Polarity-Independent Excitation of Auditory Neurons

As described with respect to examples 300 (FIG. 3) and 400 (FIG. 4), channel interference can be difficult to identify and/or characterize in some situations because of the polarity-dependent nature of the neural excitation caused by stimulation signals. The difficulty increases when more channels are activated at the same time (or close to the same time), when the channel configurations become more complex (e.g., bipolar, tripolar, phased array), and/or when the electrodes become spaced more closely together. As a result, it can be very difficult to identify and/or characterize the degree to which multiple channels may interact based on polarity-dependent neural excitation.

But if channel interactions can be identified and/or characterized more readily, then channel configurations and stimulation channel parameters can be more finely-tuned to a particular prosthesis recipient. Fine-tuning channel configurations and stimulation channel parameters to avoid, to counteract, or perhaps to even take advantage of channel interactions may enable some hearing prostheses to implement more advanced and/or complex sound encoding schemes. For example, such sound encoding schemes may allow a hearing prosthesis to precisely focus the current corresponding to a particular stimulation channel to a much smaller region of the prosthesis recipient's cochlea, resulting in better spectral resolution and a corresponding improvement in the prosthesis recipient's total hearing experience.

The difficulty of identifying and/or characterizing the interaction between multiple channels may be solved or at least ameliorated in some embodiments by using a special stimulation signal configured to cause a polarity-independent excitation in an auditory neuron. This type of special stimulation signal is referred to herein as a perturber signal, as will be described later. A perturber signal may be used in connection with a separate probe signal on two different channels to assess whether and the extent to which the two channels may interact. For example, in one embodiment, a probe signal (similar to the stimulation signals shown and described with respect to FIGS. 2-4) may be applied to an area of auditory neurons via a first channel, and a perturber signal may be applied to the area of auditory neurons via a second channel.

Figure 5A:
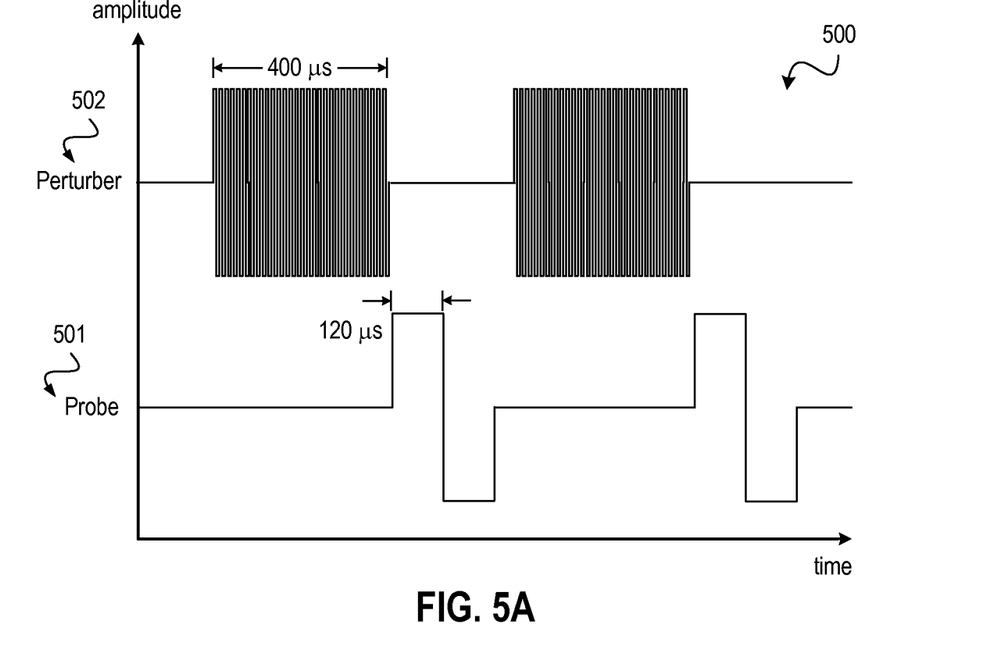
FIGS. 5A and 5B show examples of probe and perturber signals for use in identifying and/or characterizing channel interaction between two channels of a hearing prosthesis according to some embodiments of the disclosed systems, methods, and articles of manufacture.
Figure 5B:
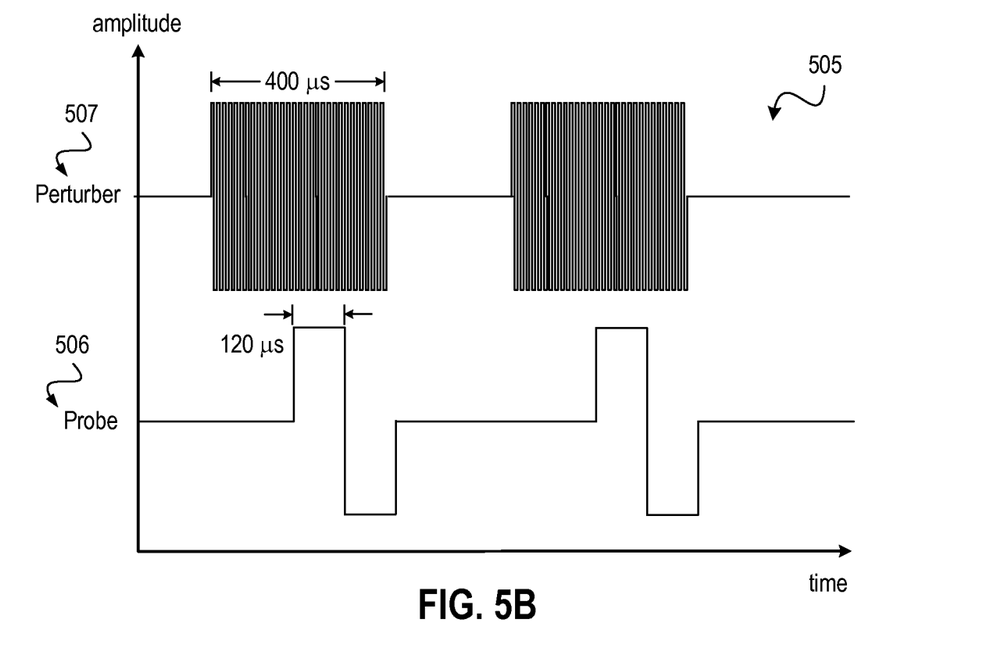

FIGS. 5A and 5B show examples of probe and perturber signals for use in identifying and/or characterizing channel interaction between two channels of a hearing prosthesis according to some embodiments of the disclosed systems, methods, and articles of manufacture. FIG. 5A shows one example 500 of a probe signal 501 and perturber signal 502 for use in identifying and/or characterizing the interaction between two channels of a hearing prosthesis according to some embodiments. FIG. 5B shows another example 505 of a probe signal 506 and a perturber signal 507 for use in identifying and/or characterizing the interaction between two channels of a hearing prosthesis according to other embodiments.

In operation, a probe signal may be applied to an area or region of auditory neurons via a first channel of the hearing prosthesis. The probe signal may be similar to the stimulation signals described herein with respect to FIGS. 2, 3, and 4. Similarly, the first channel of the hearing prosthesis may be similar to any of the channels shown and described herein, such as, for example, (i) bipolar channels 201 and 301 shown and described herein with respect to FIGS. 2 and 3, (ii) tripolar channels 403 and 408 shown and described herein with respect to FIG. 4, and/or (iii) other channel configurations, such phased arrays or other complex channel configurations.

The perturber signal may be a stimulation signal configured to cause a polarity-independent neural excitation in the auditory neurons. Similarly, the second channel of the hearing prosthesis may be similar to any of the channels shown and described herein, such as, for example, (i) bipolar channels 201 and 301 shown and described herein with respect to FIGS. 2 and 3, (ii) tripolar channels 403 and 408 shown and described herein with respect to FIG. 4, and/or (iii) other channel configurations, such phased arrays or other complex channel configurations.

In operation, the perturber signal may take advantage of a rectification effect experienced by an auditory neuron in the presence of a current corresponding to a high-frequency signal. In the presence of a current corresponding to certain high-frequency signals, an auditory neuron may experience a rectification effect that is somewhat similar (although not identical) to that of a semiconductor diode. For example, in the presence of a current corresponding to a certain high-frequency signal, the current-voltage relationship of the rectification effect experienced by the auditory neuron is non-linear and exhibits hysteresis. As a result, when the auditory neuron is exposed to the current corresponding to the high-frequency signal, the voltage across the auditory neuron may "ratchet" on successive cycles in the depolarizing (excitatory) direction, thereby causing an excitatory effect on all regions of the auditory neuron exposed to the current corresponding to the high-frequency signal.

As shown in examples 500 and 505, the perturber signal may be a high-frequency signal that causes the above-described rectification effect in an auditory neuron. In operation, the frequency of the perturber signal should be sufficiently high that it causes a polarity-independent excitation in an auditory neuron. In some embodiments, the frequency of the perturber signal may be greater than the frequency of the probe signal. For example, in some embodiments, the perturber signal may have a frequency of greater than about 20 kHz. In some embodiments, the frequency of the perturber signal may be any frequency in the range from about 20 kHz to about 55 kHz.

For some prosthesis recipients, the polarity-independence of the neural excitation may be stronger at higher frequencies, but the stimulation efficiency at higher frequencies may be lower than the stimulation efficiency at lower frequencies. In some embodiments, the polarity-independence of the neural excitation may be improved by applying a gradual onset and/or offset envelope to the perturber signal. In some embodiments, the gradual onset and/or offset envelope may be a cosine ramp, but other onset and/or offset envelopes may be used as well, including but not limited to linear ramps, cosine-squared ramps, or sigmoidal ramps for example.

In some embodiments, such as example 500 of FIG. 5A, the probe signal 501 and the perturber signal 502 may not overlap in time. In other embodiments, such as example 505 shown in FIG. 5B, the perturber signal 507 may completely overlap the probe signal 506 in time. In still other embodiments, the probe signal and the perturber signal may at least partially overlap in time. In some embodiments, the probe signal and the perturber signal may be applied at substantially the same time. In other embodiments, the probe signal and the perturber signal may be applied at different times.

In operation, the perturber signal may have an amplitude and duration that is sufficient to cause a polarity-independent neural excitation. In some embodiments, the amplitude of the perturber signal may be anywhere in the range of from about 10 μA to about 1.75 mA (or 1750 μA), but the perturber signal could have other amplitudes as well. Also, in some embodiments, the perturber signal may include a single signal burst for a predetermined duration. For example, the perturber signal may include one signal burst of about 400 μs in duration. However, the signal burst may have a shorter or longer duration than 400 μs. In other embodiments, such as examples 500 and 505 shown in FIGS. 5A and 5B, the perturber may include multiple signal bursts. The multiple signal bursts may be in regular intervals in some embodiments. But in other embodiments, the multiple signal bursts may be in irregular intervals. In some embodiments, the perturber signal may have the same duration as the probe signal. But in other embodiments, the probe and perturber signals may have different durations.

Figure 6:
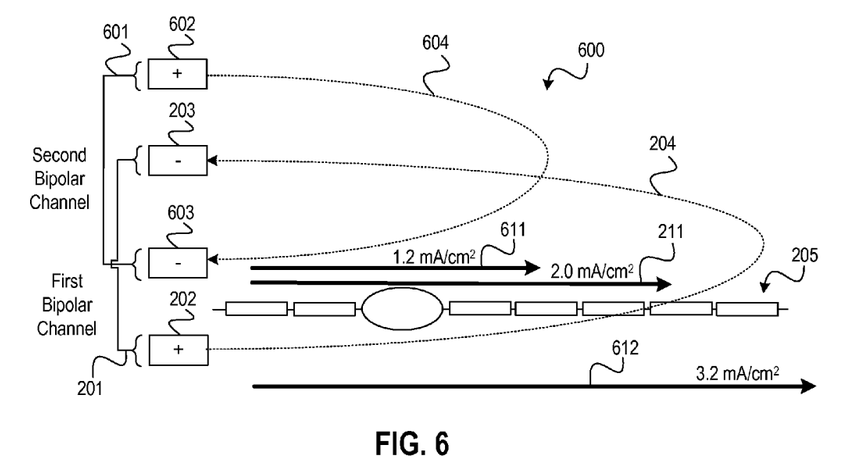
FIG. 6 shows an example of an auditory neuron in the presence of a first current corresponding to a probe signal and second current corresponding to a perturber signal applied via two bipolar channels of a hearing prosthesis according to some embodiments of the disclosed systems, methods, and articles of manufacture.

Identifying Channel Interaction with Polarity-Independent Excitation of Auditory Neurons FIG. 6 shows an example 600 of an auditory neuron 205 in the presence of current 204 corresponding to a probe signal and current 604 corresponding to a perturber signal applied via two bipolar channels 201, 601 of a hearing prosthesis according to some embodiments of the disclosed systems, methods, and articles of manufacture. In example 600, the first bipolar channel 201 is configured to apply the probe signal, and the second bipolar channel 601 is configured to apply the perturber signal.

The first bipolar channel 201 and the second bipolar channel 601 of example 600 may be substantially similar to the other bipolar channels shown and described elsewhere herein, such as the bipolar channels shown and described in FIGS. 2-3. For example, the first bipolar channel 201 includes one active electrode 202 (the current source) and one reference electrode 203 (the current sink). Similarly, the second bipolar channel 601 includes one active electrode 602 (the current source) and one reference electrode 603 (the current sink). The roles of source and sink may be reversed when the direction of current flow reverses from time to time as described elsewhere herein.

The probe signal applied via the first bipolar channel 201 of example 600 may be substantially similar to the probe signals shown and described herein with respect to FIGS. 5A and 5B. The probe signal of example 600 may also be similar to the stimulation signals shown and described herein with respect to FIGS. 2-4. In example 600, the radial component 211 of the current 204 corresponding to the probe signal is 2.0 mA/cm$^2$ flowing left to right, i.e., from the peripheral axon to the central axon of the auditory neuron 205.

The perturber signal applied via the second bipolar channel 601 of example 600 may be substantially similar to any of the perturber signals shown and described herein with respect to FIGS. 5A and 5B. In particular, the perturber signal may be configured to cause a polarity-independent excitation in the auditory neuron 205 by periodically reversing direction at a high frequency. In example 600, the radial component 611 of the current 604 corresponding to the perturber signal is 1.2 mA/cm$^2$ flowing back-and-forth, i.e., between the peripheral axon and the central axon of the auditory neuron 205. Because the perturber signal reverses direction at a high frequency to cause a polarity-independent excitation in the auditory neuron 205, it acts to depolarize, and thus excite the auditory neuron 205 at all regions where it influences the auditory neuron 205. In example 600, the auditory neuron 205 experiences the combination of: (1) the left-to-right-flowing 2.0 mA/cm$^2$ radial component 211 of the current 204 corresponding to the probe signal; and (2) the rapidly reversing 1.2 mA/cm$^2$ radial component 311 of the current 304 corresponding to the perturber signal. The left-to-right-flowing 2.0 mA/cm$^2$ radial component 211 of the current 204 corresponding to the probe signal acts to depolarize (excite) the neuron 205 at the central axon 208. The rapidly reversing flow of the current 604 corresponding to the perturber signal acts to depolarize (excite) the auditory neuron 205 at both its peripheral 207 and central axons 208. Thus the perturber signal interferes constructively with the probe signal wherever the probe signal acts to excite the auditory neuron 205. When the current 204 corresponding to the probe signal reverses direction, as may happen from time to time, it will act to depolarize (excite) the auditory neuron 205 at its peripheral axon 207 and hyperpolarize the auditory neuron 205 at its central axon 208. However, the rapidly reversing current 604 corresponding to the perturber signal still acts to excite the auditory neuron 205 at both the peripheral 207 and central axons 208, thus still interacting constructively with probe current 204 to excite the auditory neuron 205.

Because the perturber signal is configured to cause a polarity-independent depolarization (excitation) in the auditory neuron 205, the current 604 corresponding to the perturber signal increases the depolarizing (excitatory) influence of the probe signal regardless of where on the auditory neuron 205 the probe signal acts to depolarize it. As a result, the interaction between the first bipolar channel 201 and the second bipolar channel 601 can be identified and/or otherwise characterized.

In some embodiments, the interaction between the two bipolar channels 201 and 601 can be identified and/or characterized by assessing behavioral feedback from the prosthesis recipient. For example, if the two bipolar channels 201 and 601 interact, then the auditory sensation experienced by the prosthesis recipient when both the first bipolar channel 201 and the second bipolar channel 601 are activated should be greater than (i.e., sound louder than) the auditory sensation experienced by the prosthesis recipient when only the first bipolar channel 201 is activated because the perturber signal acts in concert with the probe signal to depolarize the auditory neuron 205. Thus, if the prosthesis recipient experiences an auditory sensation from the activation of both the probe and perturber signals (at the same time or close to the same time) that is greater than (i.e., louder than) the auditory sensation from the activation of the probe signal alone, then it is likely that the first bipolar channel 201 interacts with the second bipolar channel 601.

The interaction between the two bipolar channels 201 and 601 can alternatively or additionally be identified and/or characterized by assessing a reflex of the prosthesis recipient, such as the stapedius reflex. The stapedius reflex is an involuntary muscle contraction that may occur in the middle ear of some prosthesis recipients in response to a high-intensity sound. The stapedius reflex in a prosthesis recipient can be monitored by a number of different methods, including an electromyogram to estimate the onset and strength of the stapedius reflex, a middle ear immittance or tympanometry measurement, or other stapedius reflex measurements. For example, a first measure of the stapedius reflex in response to the application of the probe signal can be made, and then a second measure of the stapedius reflex in response to the application of both the probe signal and the perturber signal (at the same time or close to the same time) can be made. If the intensity of the second stapedius reflex measurement is greater than the intensity of the first stapedius reflex measurement, or if the second measurement detects an actual stapedius reflex when the first measurement fails to detect an actual stapedius reflex, then it is likely that the first bipolar channel 201 interacts with the second bipolar channel 601.

In still other embodiments, the interaction between the two bipolar channels 201 and 601 can additionally or alternatively be identified and/or characterized by an electrophysiological measurement, such as, for example, a measure of an electrically evoked compound action potential (ECAP) in response to the probe and perturber signals. For example, a first measure of the ECAP in response to the application of the probe signal can be made, and then a second measure of the ECAP in response to the application of both the probe signal and the perturber signal (at the same time or close to the same time) can be made. If the intensity of the second ECAP measurement is greater than the intensity of the first ECAP measurement, or if the second ECAP measurement detects an actual ECAP when the first ECAP measurement fails to detect an ECAP, then it is likely that the first bipolar channel 201 interacts with the second bipolar channel 601.

In still further embodiments, the perturber signal may be applied a short time prior to the probe signal. In these embodiments, a reduced response rather than an increased response may indicate a channel interaction. For example, with reference to embodiments where the interaction may be identified and/or characterized by assessing behavioral feedback from the prosthesis recipient, a perturber signal may be applied to a region of auditory neurons shortly before applying the probe signal to auditory neurons in the region affected by the perturber signal. In such a situation, some of the neurons that would have ordinarily responded to the probe signal may not respond to the probe signal because the neurons may be refractory to further excitation for a period of time (typically about 5 ms) after responding to the perturber signal. As a result, if the two bipolar channels 201 and 601 interact, then the auditory sensation experienced by the prosthesis recipient when the perturber signal is activated a short time before the probe signal may be less than (i.e., sound softer than) the auditory sensation experienced by the prosthesis recipient when only probe signal is active via the first bipolar channel 201 because of the neurons in the region affected by the perturber signal may be refractory to further excitation by the application of the probe signal. Similar decreases may be observed in embodiments that may rely on reflex measurements or electrophysiological measurements to identify and/or characterize channel interactions.

Figure 7A:
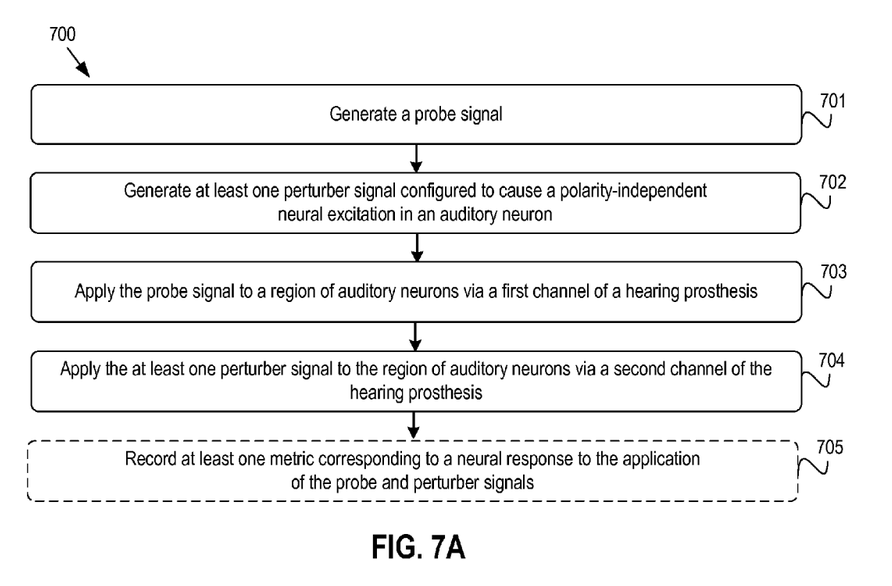
FIG. 7A shows an example method for identifying and/or characterizing channel interaction between two channels of a hearing prosthesis according to some embodiments of the disclosed systems, methods, and articles of manufacture.

Example Methods for Identifying Channel Interaction with Polarity-Independent Excitation of Auditory Neurons FIG. 7A shows an example method 700 for identifying and/or characterizing channel interaction between two channels of a hearing prosthesis according to some embodiments of the disclosed systems, methods, and articles of manufacture. In some embodiments, the hearing prosthesis may be a cochlear implant, such as cochlear implant 100 shown and described with respect to FIG. 1

At method block 701, a probe signal may be generated. The probe signal of method block 701 may be similar to any of the probe signals described herein with respect to FIG. 5A, 5B, or 6, or any of the stimulation signals described herein with respect to FIGS. 2-4. At method block 702, a perturber signal may be generated. The perturber signal may be configured to cause a polarity-independent neural excitation in an auditory neuron. In operation, the perturber signal of method block 702 may be similar to, and have any of the characteristics of, any of the perturber signals described herein with respect to any of FIG. 5A, 5B, or 6.

At method block 703, the probe signal of method block 701 may be applied to auditory neurons via a first channel of a hearing prosthesis, such as cochlear implant 100 shown and described herein with respect to FIG. 1. At method block 704, the perturber signal of method block 702 may be applied to the auditory neurons via a second channel of the hearing prosthesis. The first and second channels of the hearing prosthesis may be similar to any of the bipolar, tripolar, or phased array channels described herein with respect to FIGS. 2-6.

In some embodiments, the functions of method blocks 703 and 704 may be performed at substantially the same time. In other embodiments, the functions of method blocks 703 and 704 may be performed at different times, as shown and described herein with respect to FIG. 5A, for example. In still further embodiments, the functions of method blocks 703 and 704 may at least partially overlap in time, as shown and described herein with respect to FIG. 5B.

Some embodiments may additionally include method block 705. At method block 705, at least one metric may be recorded. The recorded metric may correspond to a neural response to the application of the probe and perturber signals to the auditory neurons as described herein. In some embodiments, the recorded metric may correspond to any of behavioral feedback, an electrophysiological measure, or a reflex measure, as described herein with respect to FIG. 6.

In some embodiments, a computing device such as the implant fitting system 145 shown and described in FIG. 1, alone or in combination with one or more other processors, may be configured to perform one or more functions of method 700. In other embodiments, the sound processing unit 116 of the cochlear implant 100 shown and described in FIG. 1, alone or in combination with one or more other processors associated with the cochlear implant 100, may be configured to perform one or more functions of method 700.

Figure 7B:
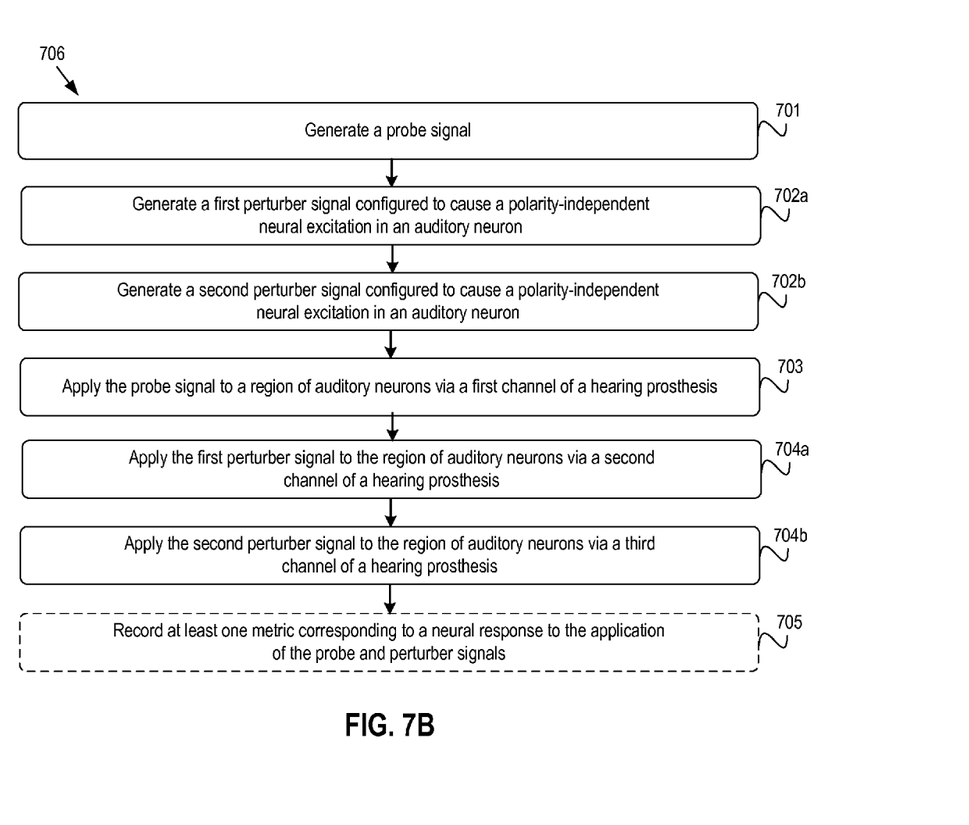
FIG. 7B shows an alternative example method for identifying and/or characterizing channel interaction between three channels of a hearing prosthesis according to some embodiments of the disclosed systems, methods, and articles of manufacture.

FIG. 7B shows an alternative example method 706 for identifying and/or characterizing channel interaction between three channels of a hearing prosthesis according to some embodiments of the disclosed systems, methods, and articles of manufacture. In some embodiments, the hearing prosthesis may be a cochlear implant, such as cochlear implant 100 shown and described with respect to FIG. 1

At method block 701, a probe signal may be generated. The probe signal of method block 701 may be similar to any of the probe signals described herein with respect to FIG. 5A, 5B, or 6, or any of the stimulation signals described herein with respect to FIGS. 2-6. At method block 702*a*, a first perturber signal may be generated, and at method block 702*b*, a second perturber signal may be generated. The first and second perturber signals may be configured to cause a polarity-independent neural excitation in auditory neurons as described herein with respect to FIGS. 5A, 5B, and 6. In operation, the first and second perturber signals of method blocks 702*a* and 702*b* may be similar to, and have any of the characteristics of, any of the perturber signals described herein with respect to any of FIG. 5A, 5B, or 6.

At method block 703, the probe signal of method block 701 may be applied to a region of auditory neurons via a first channel of a hearing prosthesis, such as cochlear implant 100 shown and described herein with respect to FIG. 1. At method block 704*a*, the first perturber signal of method block 702*a* may be applied to the auditory neurons via a second channel of the hearing prosthesis, and at method block 704*b*, the second perturber signal of method block 702*b* may be applied to the auditory neurons via a third channel of the hearing prosthesis. The first, second, and third channels of the hearing prosthesis may be similar to any of the bipolar, tripolar, or phased array channels described herein with respect to FIGS. 2-6.

In some embodiments, the functions of method blocks 703, 704*a*, and 704*b* may be performed at substantially the same time. In other embodiments, the functions of method blocks 703, 704*a*, and 704*b* may be performed at different times, similar to example 500 shown and described herein with respect to FIG. 5A, for example. In still further embodiments, the functions of method blocks 703, 704*a*, and 704*b* may at least partially overlap in time, similar to method 505 shown and described herein with respect to FIG. 5B.

Some embodiments may additionally include method block 705. At method block 705, at least one metric may be recorded. The recorded metric may correspond to a neural response to the application of the probe and perturber signals to the auditory neurons. In some embodiments, the recorded metric may correspond to any of behavioral feedback, an electrophysiological measure, or a reflex measure, as described herein with respect to FIG. 6.

In some embodiments, a computing device such as the implant fitting system 145 shown and described in FIG. 1, alone or in combination with one or more other processors, may be configured to perform one or more functions of method 706. In other embodiments, the sound processing unit 116 of the cochlear implant 100 shown and described in FIG. 1, alone or in combination with one or more other processors associated with the cochlear implant 100, may be configured to perform one or more functions of method 706.

Figure 8:
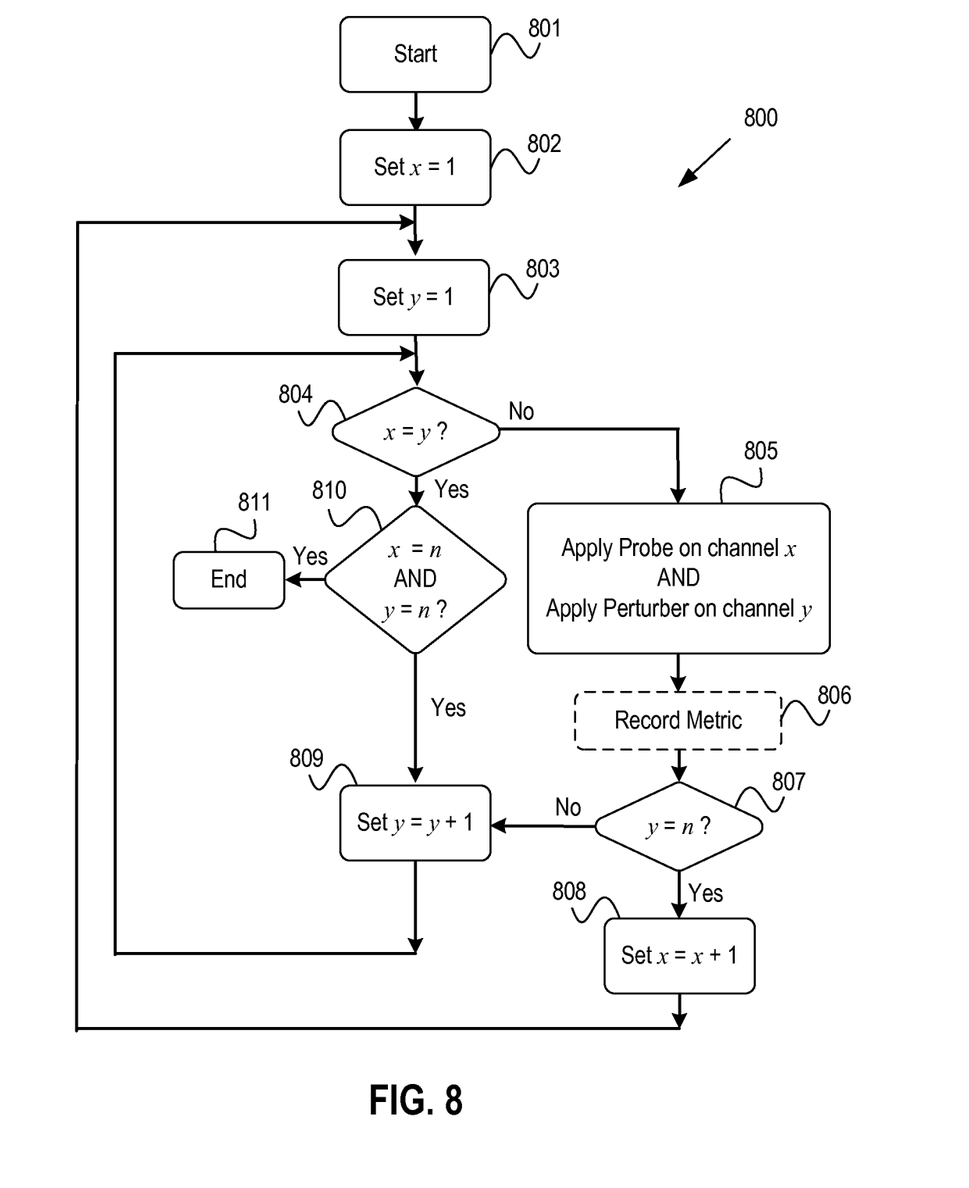
FIG. 8 shows an example algorithm for identifying and/or characterizing channel interaction between multiple channels of a hearing prosthesis according to some embodiments of the disclosed systems, methods, and articles of manufacture.

Algorithms for Identifying Channel Interaction with Polarity-Independent Excitation of Auditory Neurons FIG. 8 shows an example algorithm 800 for identifying and/or characterizing channel interaction between multiple channels of a hearing prosthesis according to some embodiments of the disclosed systems, methods, and articles of manufacture.

Algorithm 800 may start at block 801. At block 802, the x variable may be set to a value of 1, and at block 803, the y variable may be set to a value of 1. The x and y variables may correspond to channel numbers for first and second channels of a hearing prosthesis, such as cochlear implant 100 shown and described herein with respect to FIG. 1. The first and second channels of the hearing prosthesis may be similar to any of the bipolar, tripolar, or phased array channels described herein with respect to FIGS. 2-6.

At block 804, a comparison is made between the value of the x variable and the value of the y variable. If the x variable and the y variable have the same value, then the algorithm 800 may advance to block 810. At block 810, the value of the x variable is compared to a number n, and the value of the y variable is compared to the number n. The number n may correspond to the total number of channels of the hearing prosthesis. If both the value of the x variable and the value of y variable are equal to n, then the algorithm may end at block 811. But if either the value of the x variable or the value of the y variable is not equal to the number n, then the algorithm may proceed to block 809.

At block 809, the value of the y variable is incremented by 1, and the algorithm 800 returns to block 804, where a comparison is again made between the value of the x variable and the value of the y variable. If the value of the x variable does not equal the value of the y variable, then the algorithm 800 may proceed to block 805.

At block 805, a probe signal may be applied via channel x, and a perturber signal may be applied via channel y. The probe signal of block 805 may be similar to any of the probe signals described herein with respect to FIG. 5A, 5B, 6, or 7 or any of the stimulation signals described herein with respect to FIGS. 2-6. The perturber signal may be configured to cause a polarity-independent neural excitation in an auditory neuron. In operation, the perturber signal may be similar to (and have any of the characteristics of) any of the perturber signals described herein with respect to any of FIG. 5A, 5B, 6, or 7.

In some embodiments, the algorithm 800 may also include method block 806. At block 806, a metric may be recorded. The recorded metric may correspond to a neural response to the application of the probe and perturber signals in block 805. In some embodiments, the recorded metric may correspond to any of behavioral feedback, an electrophysiological measure, or a reflex measure, as described herein with respect to FIG. 6.

In embodiments of the algorithm 800 that include method block 806, the algorithm may proceed to block 807 after recording the metric at block 806. But in embodiments of the algorithm 800 that may not include block 806, the algorithm may proceed to block 807 after applying the probe and perturber signals at block 805.

At block 807, the value of the y variable is compared to the number n corresponding to the number of channels of the hearing prosthesis. If the value of the y variable is not equal to n, then the algorithm 800 may proceed to block 809. At block 809, the value of the y variable is incremented by 1, and the algorithm 800 may then return to block 804 again. But if the value of the y variable is equal to n, then the algorithm 800 may proceed to block 808. At block 808, the value of the x variable is incremented by 1, and the algorithm 800 may return to block 803.

In operation, algorithm 800 may be executed as part of a fitting procedure where channel interaction between multiple pairs of channels of the hearing prosthesis may be identified and/or characterized in a systematic fashion. For example, the probe signal may be activated on channel 1 (i.e., when the value of the x variable is 1) while the perturber signal may be activated on channels 2-n (i.e., the value of the y variable is incremented from 2 through n as the algorithm follows the path through blocks 805, 806, 807, 809, 804, and then back to 805). After activating the probe signal on channel 1 and the perturber signal on every other channel, the algorithm 800 may then proceed to activate the probe signal on channel 2 and the perturber signal on every other channel. Algorithm 800 may continue in this or a similar fashion until the probe and perturber signals have been activated on all of the combinations of channels of the hearing prosthesis.

Although algorithm 800 is shown with only two variables, x and y, corresponding to two channels, alternative embodiments could add additional variables corresponding to additional channels along with nested loops to activate individual combinations of the multiple channels to determine which channel combinations caused interference. Similarly, other algorithms for identifying and/or characterizing channel interaction could be used as well.

Computer Readable Media Implementations

In some embodiments, the disclosed features and functions of the systems, methods, and algorithms shown and described herein may be implemented as computer program instructions encoded on a computer readable media in a machine-readable format.

Figure 9:
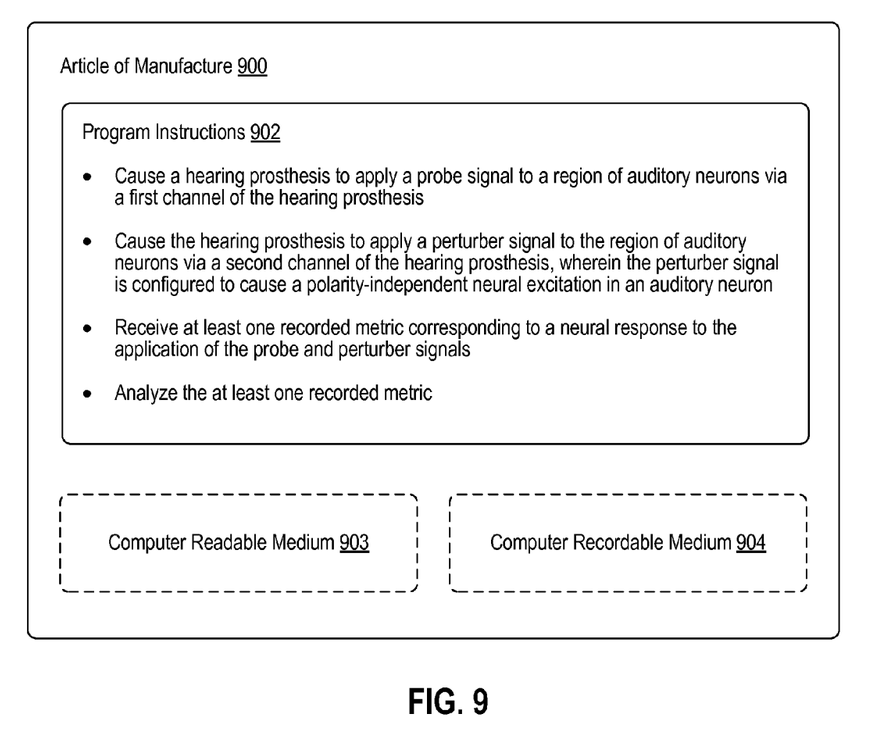
FIG. 9 shows an example of an article of manufacture including computer readable media with instructions for causing one or more processors to execute a method for identifying and/or characterizing channel interaction between hearing prosthesis channels according to some embodiments of the disclosed systems and methods.

FIG. 9 shows an example of an article of manufacture 900 including computer readable media with instructions for causing one or more processors to execute a method for identifying and/or characterizing channel interaction between hearing prosthesis channels according to some embodiments of the disclosed systems and methods. FIG. 9 shows a schematic illustrating a conceptual partial view of an example article of manufacture 900 that may include computer program instructions 902 for executing a computer process on a computing device, arranged according to at least some embodiments described herein.

In some examples, the article of manufacture 900 may include a computer-readable medium 903, such as, but not limited to, a hard disk drive, a Compact Disc (CD), a Digital Video Disk (DVD), a digital tape, flash memory, etc. In some implementations, the article of manufacture 600 may include a computer recordable medium 604, such as, but not limited to, a hard disk drive, a Compact Disc (CD), a Digital Video Disk (DVD), a digital tape, flash memory, etc.

The one or more programming instructions 902 may be, for example, computer executable and/or logic implemented instructions. In some embodiments, a computing device such as the implant fitting system 145 shown and described in FIG. 1, alone or in combination with one or more additional processors or computing devices, may be configured to perform certain operations, functions, or actions to implement the features and functionality of the disclosed systems and methods based at least in part on the programming instructions 902. In still other embodiments, the sound processing unit 116 of the cochlear implant 100, alone or in combination with one or more other processors associated with the cochlear implant 100, may be configured to perform various operations, functions, or actions to implement the features and functionality of the disclosed systems and methods based at least in part on the programming instructions 902.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A method comprising:
    generating a probe signal configured to cause a polarity-dependent neural excitation in an auditory neuron;
    generating at least one perturber signal configured to cause a polarity-independent neural excitation in an auditory neuron;
    applying the probe signal to a region of auditory neurons via a first channel of a hearing prosthesis; and
    applying the at least one perturber signal to the region of auditory neurons via a second channel of the hearing prosthesis.

2. The method of claim 1, wherein the perturber signal has a frequency greater than about 20 kHz.

3. The method of claim 1, wherein the probe signal and the perturber signal are applied to the region of auditory neurons at substantially the same time.

4. The method of claim 1, wherein the probe signal and the perturber signal are applied to the region of auditory neurons at different times, and wherein the probe signal and the perturber signal at least partially overlap in time.

5. The method of claim 1, wherein the first channel of the hearing prosthesis comprises at least one active electrode and at least one reference electrode, and wherein the second channel of the hearing prosthesis comprises at least one active electrode and at least one reference electrode.

6. The method of claim 1, further comprising:
    generating at least one additional perturber signal configured to cause a polarity-independent neural excitation in an auditory neuron; and
    applying the at least one additional perturber signal to the region of auditory neurons via a third channel of the hearing prosthesis.

7. The method of claim 1, wherein the perturber signal comprises one of a rectangular waveform, a sinusoidal waveform, and a triangular waveform.

8. The method of claim 1, wherein the perturber signal is a single burst of defined duration.

9. The method of claim 1, wherein the perturber signal comprises a plurality of bursts.

10. The method of claim 1, wherein the perturber signal is amplitude-modulated by at least one of a cosine onset ramp and a cosine offset ramp.

11. The method of claim 1, further comprising:
    recording one or more metrics corresponding to a neural response to the application of the probe and perturber signals.

12. The method of claim 11, wherein the metric is at least one of a behavioral feedback, an electrophysiological feedback, and a reflex measure.

13. A system comprising:
    a first channel comprising a first set of one or more electrodes;
    a second channel comprising a second set of one or more electrodes; and
    one or more processors configured to:
        cause a probe signal to be applied to a region of auditory neurons via the first channel, wherein the probe signal is configured to cause a polarity-dependent neural excitation in an auditory neuron; and
        cause a perturber signal to be applied to the region of auditory neurons via the second channel, wherein the perturber signal is configured to cause a polarity-independent neural excitation in an auditory neuron.

14. The system of claim 13, wherein the perturber signal has a frequency between about 20 kHz and 55 kHz.

15. The system of claim 13, wherein the one or more processors are configured to cause the probe signal and perturber signal to be applied to the region of auditory neurons at substantially the same time.

16. The system of claim 13, wherein the one or more processors are configured to cause the probe signal and the perturber signal to be applied to the region of auditory neurons at different times.

17. The system of claim 13, further comprising:
    a third channel comprising a third set of one or more electrodes, wherein the one or more processors are configured to cause an additional perturber signal to be applied to the region of auditory neurons via the third channel, and wherein the additional perturber signal is configured to cause a polarity-independent neural excitation in an auditory neuron.

18. The system of claim 13, wherein the perturber signal comprises one of a rectangular waveform, a sinusoidal waveform, and a triangular waveform.

19. The system of claim 13, wherein the perturber signal comprises at least one of a single burst of defined duration or a plurality of bursts.

20. The system of claim 13, wherein the perturber signal is amplitude-modulated by at least one of a cosine onset ramp and a cosine offset ramp.

21. An article of manufacture comprising a computer readable media with instructions encoded thereon, the instructions comprising:
    instructions for causing a hearing prosthesis to apply a probe signal to a region of auditory neurons via a first channel of the hearing prosthesis, wherein the probe signal is configured to cause a polarity-dependent neural excitation in an auditory neuron; and
    instructions for causing the hearing prosthesis to apply a perturber signal to the region of auditory neurons via a second channel of the hearing prosthesis, wherein the perturber signal is configured to cause a polarity-independent neural excitation in an auditory neuron.

22. The article of manufacture of claim 21, wherein the perturber signal has a frequency greater than about 20 kHz.

23. The article of manufacture of claim 21, wherein the instructions further comprise:

instructions to cause the hearing prosthesis to apply the probe signal and the perturber signal to the region of auditory neurons at substantially the same time.

24. The article of manufacture of claim 21, wherein the instructions further comprise:
   instructions for causing the hearing prosthesis to apply the probe signal and the perturber signal to the region of auditory neurons at different times.

25. The article of manufacture of claim 21, wherein the instructions further comprise:
   instructions for causing the hearing prosthesis to apply at least one additional perturber signal to the region of auditory neurons via at least one additional corresponding channel of the hearing prosthesis, wherein the at least one additional perturber signal is configured to cause a polarity-independent neural excitation in an auditory neuron.

26. The article of manufacture of claim 21, wherein the perturber signal comprises one of a square waveform, a rectangular waveform, a sinusoidal waveform, and a triangular waveform.

27. The article of manufacture of claim 21, wherein the perturber signal comprises at least one of a single burst of defined duration or a plurality of bursts.

28. The article of manufacture of claim 21, wherein the perturber signal is amplitude-modulated by at least one of a cosine onset ramp and a cosine offset ramp.

29. The article of manufacture of claim 21, wherein the instructions further comprise:
   instructions for recording a first metric corresponding to a neural response to the application of the probe signal;
   instructions for recording a second metric corresponding to a neural response to the application of the probe signal and the perturber signal; and
   instructions for comparing the first and second metrics.

30. The article of manufacture of claim 29, wherein the at least one recorded metric is at least one of a behavioral feedback, an electrophysiological feedback, and a reflex measure.

* * * * *